United States Patent
Slautterback et al.

(10) Patent No.: US 7,572,241 B2
(45) Date of Patent: Aug. 11, 2009

(54) ORTHOPEDIC NIGHT FOOT SPLINT

(75) Inventors: E. Gerald Slautterback, Pinehurst, NC (US); Rhonda Machin Newman, Weston, FL (US); Daniel J. Bozza, Coral Springs, FL (US)

(73) Assignee: BSN Medical, Inc., Charlotte, NC (US)

( * ) Notice: Subject to any disclaimer, the term of this patent is extended or adjusted under 35 U.S.C. 154(b) by 369 days.

(21) Appl. No.: 11/701,772

(22) Filed: Feb. 2, 2007

(65) Prior Publication Data

US 2007/0142759 A1 Jun. 21, 2007

Related U.S. Application Data

(63) Continuation-in-part of application No. 10/851,810, filed on May 21, 2004, now Pat. No. 7,182,743, which is a continuation-in-part of application No. 10/388,689, filed on Mar. 14, 2003, now abandoned, which is a continuation-in-part of application No. 29/177,120, filed on Mar. 4, 2003, now Pat. No. Des. 481,798.

(51) Int. Cl.
   *A61F 5/00* (2006.01)
(52) U.S. Cl. ............................... 602/23; 602/27; 602/28
(58) Field of Classification Search ................... 602/23, 602/27, 28, 60, 65–66; 128/882
   See application file for complete search history.

(56) References Cited

U.S. PATENT DOCUMENTS

| | | | | |
|---|---|---|---|---|
| 5,242,379 | A | * | 9/1993 | Harris et al. .................. 602/27 |
| 5,399,155 | A | * | 3/1995 | Strassburg et al. |
| 5,486,157 | A | * | 1/1996 | DeBenedetto |
| 5,542,912 | A | * | 8/1996 | Hess |
| 5,700,237 | A | * | 12/1997 | Hess |
| 5,776,090 | A | * | 7/1998 | Bergmann et al. |
| 5,799,659 | A | * | 9/1998 | Stano |
| 5,887,591 | A | * | 3/1999 | Powell et al. |
| 5,897,520 | A | * | 4/1999 | Gerig |
| 6,019,741 | A | * | 2/2000 | Prieskom |
| 6,102,881 | A | * | 8/2000 | Quackenbush et al. |
| 6,110,078 | A | * | 8/2000 | Dyer |
| D434,504 | S | * | 11/2000 | Miller |
| 6,155,998 | A | * | 12/2000 | Gilmour ...................... 602/27 |
| 6,267,742 | B1 | * | 7/2001 | Krivosha et al. |
| 6,361,514 | B1 | * | 3/2002 | Brown et al. |
| 6,689,081 | B2 | * | 2/2004 | Bowman |

(Continued)

*Primary Examiner*—Michael A. Brown
(74) *Attorney, Agent, or Firm*—Adams Intellectual Property Law, P.A.

(57) ABSTRACT

A foot splint for the prevention and rehabilitation of plantar fasciitis by maintaining a wearer's foot and, hence, his plantar fascia in a pre-selected amount of dorsiflexion. The foot splint includes a footplate for supporting the wearer's foot, a bracket integrally attached to the footplate near the heel region, where the bracket has at least one ankle angle preset, a strut (either medial, lateral, or both sides) extending along the lower leg of the wearer, a strut sleeve removably enveloping the strut. The sleeve has an upper end and a lower end, and the strut protrudes from the lower end of the sleeves. There is an adjustable leg strap attached to the strut sleeve at the upper end. The strap secures the upper end to the leg of a wearer during operation. A padded insole may be provided to cushion the wearer's foot from the footplate. The foot splint provides a comfortable "slipper-like" feel for the wearer.

20 Claims, 7 Drawing Sheets

U.S. PATENT DOCUMENTS 6,824,523 B2 * 11/2004 Carlson
6,827,696 B1 * 12/2004 Maguire
6,858,017 B2 * 2/2005 Peters
6,976,972 B2 * 12/2005 Bradshaw .................... 602/23

* cited by examiner

ORTHOPEDIC NIGHT FOOT SPLINT

CROSS REFERENCE TO RELATED APPLICATIONS

This application is a continuation-in-part of utility application Ser. No. 10/851,810 filed on May 21, 2004 now U.S. Pat. No. 7,182,743, which is a continuation-in-part of utility application Ser. No. 10/388,689 filed on Mar. 14, 2003 now abandoned, which itself is a continuation-in-part of design application No. 29/177,120, filed Mar. 4, 2003 now U.S. Pat. No. D,481,798.

FIELD OF THE INVENTION

The present invention relates generally to orthopedic devices for rehabilitating a human foot, and more particularly to a night splint for stretching the plantar fascia of a person for the treatment of plantar fasciitis.

BACKGROUND OF THE INVENTION

The plantar fascia is a ligament structure that attaches between the calcaneous bone of the heel and the metatarsals located in the front part of the human foot. In particular, the plantar fascia maintains the arch of the foot and is placed in tension during walking and running.

Traumatic or, more typically, chronic overstressing of the plantar fascia leads to a condition commonly referred to as "plantar fasciitis". This condition is characterized by inflammation, as well as tearing and shortening of the plantar fascia through scarring. The inflammation and tearing usually occur at the point where the fascia is attached to the heel bone and can cause the growth of spike-like projections of new bone, called heel spurs.

The plantar fasciitis condition causes mild to severe pain in the heel or arch which, if left untreated, can interfere with walking and daily living activities, as well as athletic activity. This condition can afflict both athletic and sedentary persons, and is especially common in the obese and in people who exercise on hard surfaces.

The symptoms of plantar fasciitis usually occur in the morning, resulting from activity of the previous day, due to cramping and muscle tightening of the foot and leg at night while the individual is asleep. A broad range of treatments are prescribed for plantar fasciitis, depending upon the severity of the injury and length of time the condition has existed. Among commonly used treatments are rest, ice, anti-inflammatory/analgesia medication, ultrasound to decrease inflammatory response, taping, heel pads, support socks, orthopedic device, physical therapy and even surgery. The various orthosis, (e.g. device or support, especially for the foot, used to relieve or correct an orthopedic problem), include walking type splints, shoe insole inserts and night splints.

Although similar in appearance to foot and ankle casts, also called walking casts, a night splint for the treatment of plantar fasciitis is only superficially similar to a walking cast. A foot or ankle cast is made so that the force vector of the patient's weight passes vertically through the cast and the patient's leg when he is standing. In the medical industry, no walking casts are made which do not place the bottom of the patient's foot at a 90 degree angle to the patients leg, which is consistent with a vertical force vector. Thus, no walking casts are built to induce and maintain dorsiflexion or plantar flexion. In addition, a walking cast is made to provide the patient with a weight-bearing region forward of the heel, on which the weight of the body is placed when walking, and from which the patient can pivot forward when taking the next stride. The bearing and pivoting structure can be a rounded knob under the mid region of the foot, or it can be a rounded surface which covers the bottom of the cast from heel to toe. A walking cast may also have a cushioning region directly under the heel to absorb some of the shock of walking. Walking casts are not made to wear in bed at night, and are not made to induce a stretching effect on tendons. They are made to provide support to healing ankle and foot joints and bones, and to control the motion of these healing joints and bones while healing takes place.

To treat plantar fasciitis, it is necessary to use considerable force to counteract the strong muscles and tendons of the lower leg and foot. If this force is applied improperly, pressure points can result, with resulting discomfort and complications for some patients. Some patients have reduced blood circulation or sensation in the feet, such as patients with diabetes, vascular insufficiency, polio, stroke, trauma, or neurological problems. In such patients, if they need to use a night splint for treatment of plantar fasciitis, it is important to minimize the pressure points exerted by the night splint on the patient's foot, while still exerting the necessary force on the foot and lower leg structure. The night splint must also not bruise or scratch the collateral leg during sleep, must not soil or tear bedding, and must be compatible with a sleeping partner. Walking casts are not designed to accomplish these objects.

In contrast, night splints allow for rehabilitation of the plantar fascia by maintaining the foot in a dorsiflexed condition such that the plantar fascia is slightly extended and not allowed to contract during the night. Conventional night splints consist, essentially, of a boot-like structure which is strapped to a patent's lower leg and foot. Although more streamlined than walking splints, boot-like splints are still quite heavy and bulky and, as such, are uncomfortable and interfere with sleep. For example, the boot splint impedes the wearer's ease of moving between sleep positions. Moreover, the bulk of the splint may bruise or scratch the collateral leg during sleep, and may interfere with a sleeping spouse. Further, such splints encompass the ankle region of a person, and may exert pressure points on the patient's foot or lower leg structure. Such pressure point concerns are even more critical for patient's having reduced blood circulation or sensation in the feet, such as patients with diabetes, vascular insufficiency, polio, stroke, trauma, or neurological problems.

Another type of conventional night splint is a generally L-shaped brace. The top portion of the L-shaped brace is configured to fit around the rear and sides of the patient's calf, ankle and heel, while the bottom portion of the L-shaped brace extends forwardly beneath the sole of the foot. These braces are held to the foot and leg by strapping, or the like. While such splints are less bulky than boot-type splints, some patients still complain that these splints are uncomfortable, particularly when worn in bed. The rigid portion of the splint is disposed between the patient and the bed mattress in most positions and, hence, can cause pressure points at the rear and side of the heel, ankle, and lower leg.

Another type of device for maintaining a dorsiflexion of the plantar fascia ligament is described in U.S. Pat. No. 5,399,155 issued to Strassburg et al. The device consists of an over-the-calf sock, a d-ring attached to the front (shin) side, and an adjustable support strap attached to the toe portion of the sock. The support strap is passed through the d-ring loop, and secures to itself utilizing hook and loop attachment. The degree of stretch provided to the to plantar fascia ligament can be controlled by adjusting the tension provided by the support strap. Such devices do not provide any lateral support for the foot. Furthermore, tension in the support strap tends to pull the sock down the leg of the wearer, which allows the foot to relax to plantarflexed position.

Accordingly, what is needed is a night splint for the rehabilitation of plantar fasciitis that is comfortable to wear during sleeping, while maintaining the plantar fascia in a slight stretch. Further needed is for the night splint to be light weight, streamline, and have a low profile, in order to enhance comfort to the wearer.

SUMMARY OF THE INVENTION

The present invention is an orthosis foot splint for treatment and rehabilitation of plantar fascia. The foot splint is configured to maintain a wearer's foot in slight dorsiflexion in order to stretch the plantar fascia. The foot splint is lightweight, streamline, and avoids causing pressure points against the wearer's foot and leg, thus making the splint comfortable and unobtrusive to wear while resting in bed.

In addition to its use in the treatment of plantar fasciitis, the invented foot splint can be used in the treatment of calf muscle cramps, muscle tightening and runner's cramps, foot drop, paratenon tendonitis, Achilles tendonitis, heel and arch pain, pronation syndromes, calcaneal apophysitis, and post-surgical treatment of the foot.

In the broadest sense, the present invention relates to a foot splint having a footplate and a strut. The footplate and strut are hingedly attached and hold a wearer's foot in an angle in dorsiflexion. Preferably, the strut includes an opening that coincides with the ankle of the wearer to provide additional comfort to the wearer. More preferably, the strut is positionable along the side of the wearer's leg, and is enveloped in sleeve to which is attached an adjustable strap for securing the foot splint to the wearer's leg.

BRIEF DESCRIPTION OF THE DRAWINGS

The foregoing and other objects will become more readily apparent by referring to the following detailed description and to the appended drawings in which.

DETAILED DESCRIPTION

The present invention is a device for maintaining the plantar fascia in a slight stretch for the rehabilitation and relief from plantar fasciitis. The device is suitable for use anytime, but uniquely configured for comfortable wear and rehabilitation while sleeping.

Figure 1:
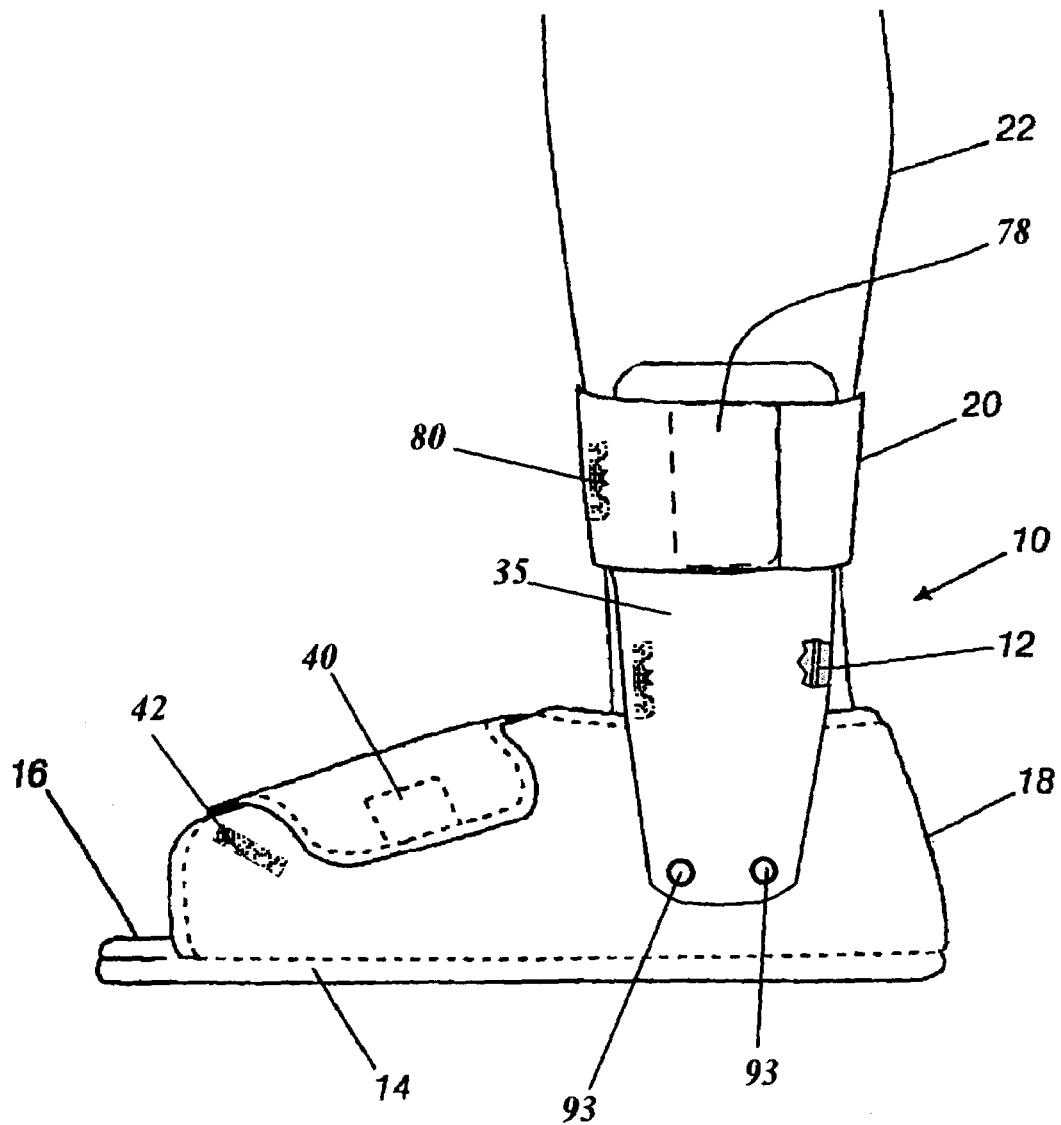
FIG. 1 is a side view of the invented foot splint, taken from the medial side of a wearer's foot, in position on the wearer's right foot.
Figure 4:
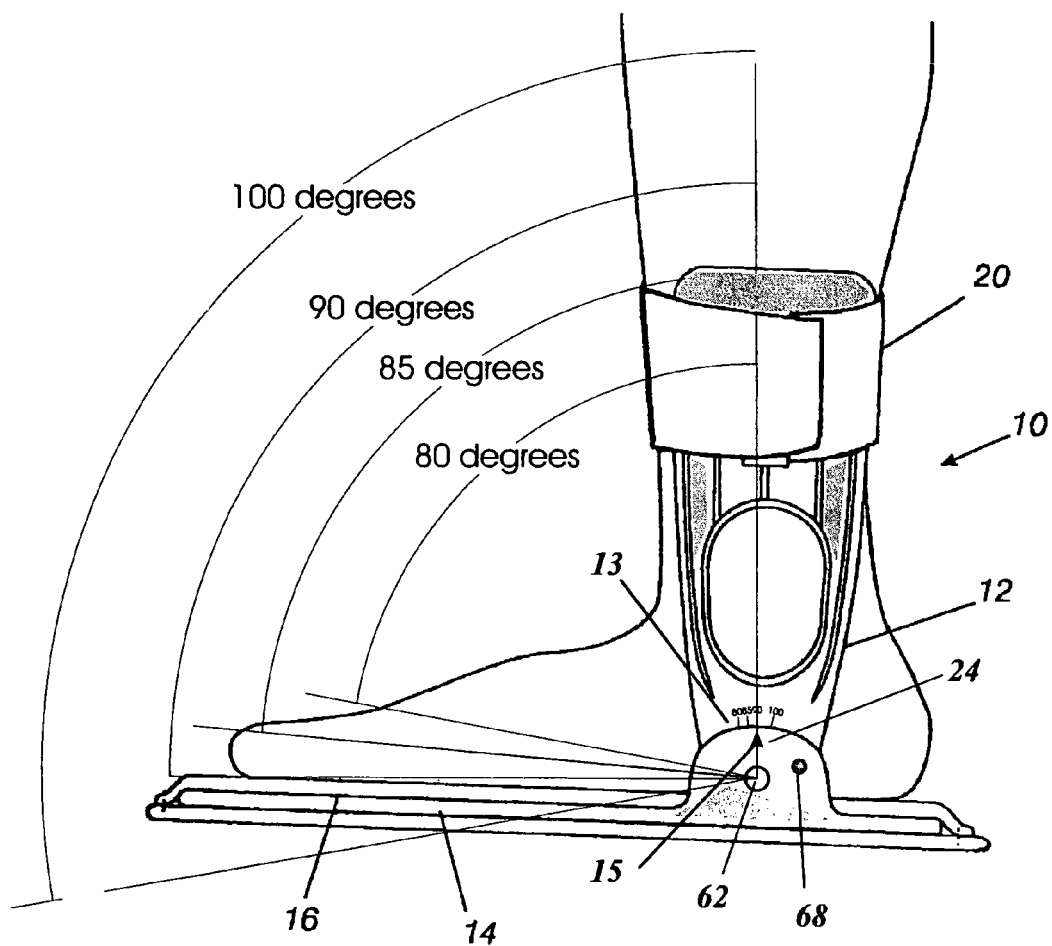
FIG. 4 is a side view of the foot splint illustrating various ankle angled presets, where the sides of the wrap and the strut sleeve are removed for illustrative purposes.

Referring now to the drawings, and particularly to FIG. 1, the invented foot splint 10 is shown in position on a wearer's foot, here the right foot. The foot splint 10 includes a strut 12 attached to a footplate 14, an insole 16 for providing a cushioning barrier between the foot and the footplate 14, a wrap 18 for holding the foot in place to the footplate 14, and a leg strap 20 with an integral a strut sleeve 35 removably enveloping the strut, where the leg strap 20 holds the strut 12 in place on the wearer's leg 22. In the FIG., a portion of the strut sleeve 35 is cut away to illustrate the strut 12 inserted into the strut sleeve 35. FIG. 4 illustrates the strut 12 of the invented splint wherein the strut sleeve is removed.

Figure 2:
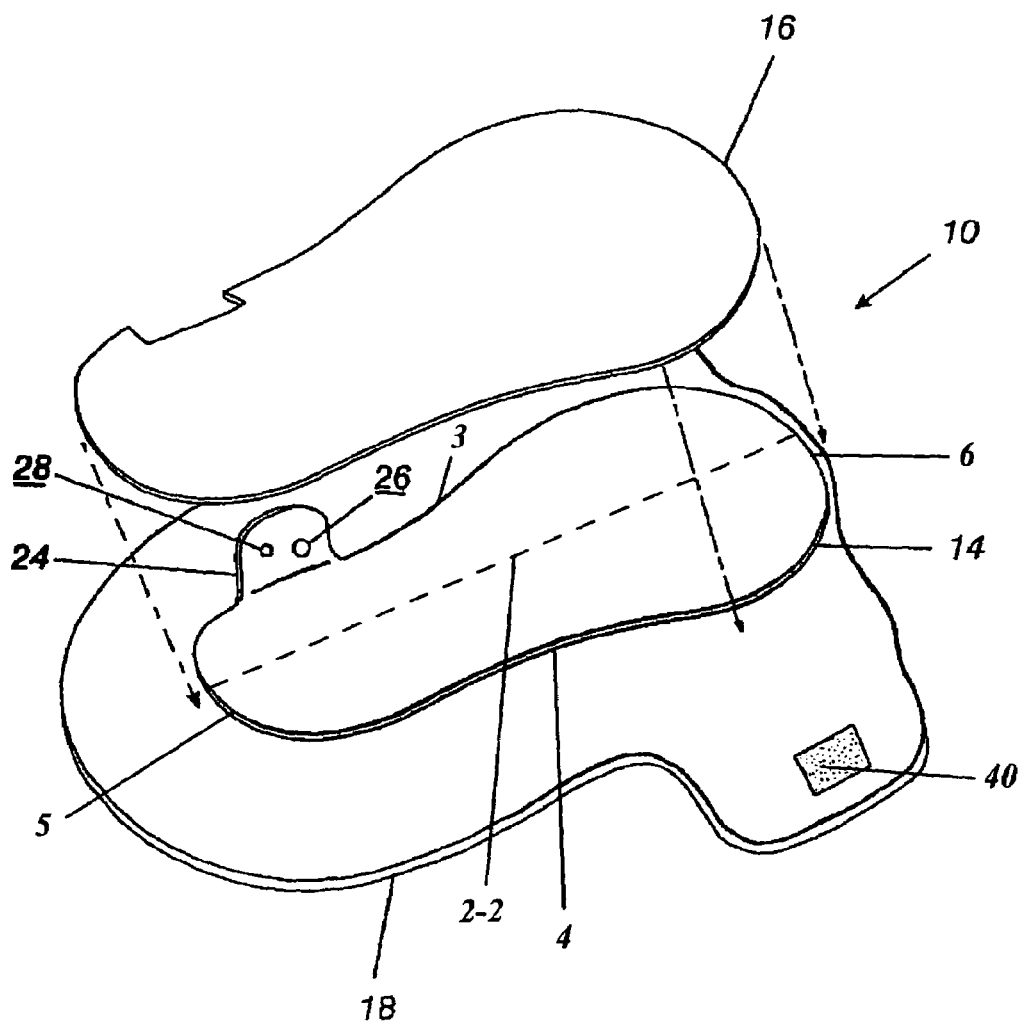
FIG. 2 is an exploded perspective view of the foot splint, partially constructed, shown without the strut.

FIG. 2 shows the foot splint 10, partially constructed, with the wrap 18 laid open and the strut removed in order to illustrated further details of the invention. The footplate 14 is shaped and sized so that the wearer's foot may be fully supported thereon. The footplate 14 is preferably constructed of relatively strong lightweight material, for instance a resilient plastic or a light weight metal or a combination thereof, to provide sufficient rigidity to support the wearer's foot. The illustrated footplate 14 has a lateral side (e.g. outside) 4, a medial side (e.g. inside) 3, a toe region 6 and a heel region 5. The footplate for the left foot would be substantially the mirror image of the illustrated right footplate. As can be seen from the drawing, the right footplate 14 is configured with a medial strut, however the footplate, except for the position of the bracket, is symmetrical along sectional line 2-2, and therefore the footplate 14 is suitable for a splint with a lateral strut for a left foot. Likewise a left footplate with a medial bracket would be suitable for a splint with a lateral strut for a right foot.

The bracket 24 extends from the medial side of the footplate 14 and forms the mounting to which the strut 12 (FIG. 1) is attached. The bracket 24 has a pivot hole 26 and a set opening 28. The pivot hole 26 defines the pivot axis between the footplate 14 and the strut 12, while the set opening 28 allows for the foot splint 10 to be set at selected degrees of dorsiflexion, as further described below. The strut 12 is preferably constructed of a relatively strong lightweight material, for instance a resilient plastic or a light weight metal or a combination thereof.

The insole 16 is sized and laid over the footplate 14 to provide a cushioning barrier between the wearer's foot and the footplate 14. In the preferred embodiment, the periphery of the insole 16 slightly overhangs the edges of the footplate 14. Stitching 30 is provided through this periphery and joins the insole 16 to the wrap 18, as shown in FIG. 3.

The wrap 18 has a portion that is positioned under the footplate 14, and side portions which conform around the sides of the wearer's foot. The bottom portion of the wrap 18 provides a cushioning barrier between the footplate 14 and the surrounding environment. The heel portion 46 of the wrap 18 may be cupped to hold the heel of the wearer's foot. The outside of the wrap is comprised of a Velcro type pile material 80. A flap portion 34 of the wrap 18 is sized to extend over the top of the foot, to the other side of the wrap 18. The flap portion 34 has a Velcro™-type hook fastener 40 which releasably fastens to the Velcro type pile material 42, and is adjustable over a wide range as the hook fastener 40 can attach to anywhere on the outside Velcro type pile material 42. The wrap 18, and particularly the flap portion 34, securely holds the wearer's foot in place against the footplate 14. The wrap 18 is generally conforming to the foot and padded. Advantageously, the wrap 18, insole 16 and footplate 14 form a comfortable, slipper-like foot enclosure.

It is noted that other means may be used to secure the wrap 18 over the foot. For example, the outer surface of the wrap 18 may be made of a Lycra.™ spandex and nylon blend having an unbroken loop construction to which the Velcro™-type hooks 40 provided on the flap portion 34 may be frictionally engaged. As another example, complementary snaps, zipper or laces may be used. However, as these attachment means are more cumbersome to use, limit the amount that the wrap can be adjusted to accommodate various foot sizes, or may cause pressure points and ridge lines and, thus, they are less preferred. As it will also be appreciated by those skilled in the art, the wrap 18 may be provided in a variety of configurations. For example, the wrap 18 may be configured so that it extends only along the sides and top of the wearer's foot, and not under the footplate 14. The splint may have a wrap strap to augment the flap, where the wrap strap reversibly and adjustably bands around the footplate and the wrap.

Figure 3:
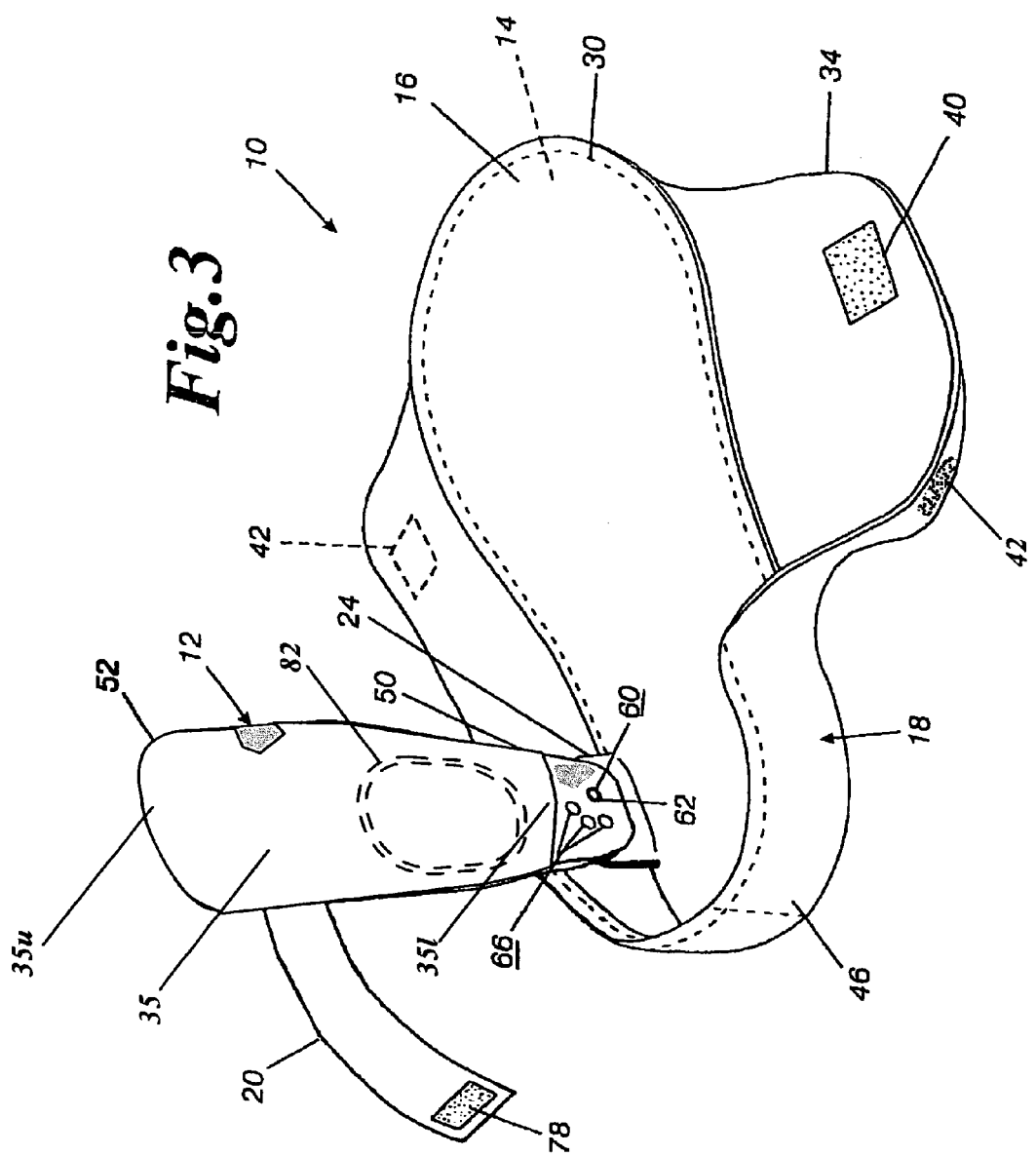
FIG. 3 is a perspective view of the foot splint, with the wrap open to receive the foot of a wearer.

FIG. 3 shows the foot splint 10 in completed form, with the medial strut 12 in place, and ready to receive the right foot of a wearer. The strut 12 extends along the medial side (inside) of the wearer's leg and has a distal section 50 attached to the footplate bracket 24 and a proximal section 52 terminating along the wearer's lower leg. The strut sleeve 35 removably envelopes the strut 12. The strut sleeve 35 comprises an upper end 35u, and a lower end 35l. The distal end of the strut is lapped by the open lower end 35l of the strut sleeve. The strut sleeve 35 provides a cushioning material on the inward facing surface of the strut 12 forming padding between the strut 12 and the wearer. The lower end 35l of the strut sleeve 35 preferably extends to the insole on the inside of the splint, providing a substantially continuous layer of padding. The outside of lower end 35l of the strut sleeve 35 is fitted with fasteners, such as snaps 93, to attach the strut sleeve to the wrap. Likewise, counterpart fastening means are on the outside of the wrap to attach to the fasteners on the strut sleeve. The overlapping lower end 35l prevents the wearer from being accidentally pinched at the junction of the strut and the bracket. The outside 80 of the strut sleeve like the wrap is comprised of a Velcro type pile material.

The distal section 50 of the strut 12 is pivotally connected to the bracket on the footplate 14. As illustrated the strut is provided with a pivot bearing hole 60, which corresponds to the bracket pivot bearing hole 28 (FIG. 2). An axial rod 62 is received through the pivot bearing holes (26,60), rotatably mounting the strut 12 to the footplate 14. The distal section 50 is provided with a plurality of radially spaced angled presets which fixes the desired amount of dorsiflexion of the foot splint 10. The angled presets comprise strut openings 66 where one is aligned with the set opening 28 (FIG. 2) in the bracket 24 by rotating the strut 12 in relation to the footplate 14 until the desired strut opening 66 is aligned with the set opening 28. An engaging locking means 68 (FIG. 4) such as set screw, a spring loaded pin, a detent, a snap rivet or other suitable device sets the angle to the desired amount of dorsiflexion of the foot splint 10. In so doing the footplate 14 and strut 12 are selectively set at an angle in relation to each other. As an example, the openings 66 allow for the foot splint 10 to be adjusted in increments between 70 and 90 degrees in order to hold the wearer's foot in incremental amounts of dorsiflexion. As illustrated in FIG. 4 the wearer can visually align the openings or select the desired angled preset using indices 13 on the strut and a pointer 15 on the bracket. In the illustrated embodiment there are 4 angled presets, three for dorsiflexion, between 80 to 90 degrees; and one angled preset that is a substantially non-stretched mode of 100 degrees. The dorsiflexion increments are nominally about 5 degrees. The nominal dorsiflexion range is from about 80 to about 90 degrees. As such, the wearer can adjust the amount of desired "stretch" at which to maintain his plantar fascia.

The strut 12 may be provided with an opening 82, shown in FIG. 4 and in ghost in FIG. 3. The opening 82 is sized and formed in the strut 12 to coincide with the malleolus anklebone of the wearer. As such, any potential pressure points between the strut 12 and ankle are obviated.

The strut 12 is releasably secured to the wearer's leg by the leg strap 20. The strap 20 with integral strut sleeve 35 is affixed to the proximal section of the strut 12. The strap is wrapped around the lower leg of the wearer, tensioned an appropriate amount, and the Velcro™-type hook fastener 78 on the inside of the strap 20 is attached to the Velcro type pile material 80 comprising the outside of the leg strap 20 (see FIG. 1 and FIG. 3).

In FIG. 4, the foot splint 10 is shown with the sides of the wrap 18 removed for illustrative purposes. As shown, the foot is held along the footplate 14, with the insole 16 providing cushioning there-between. The medial strut 12 extends along the medial side (inside) of the leg and is releaseably attached thereto by the strap 20. The engaging locking means 68 is a set screw, which is inserted through the selected set openings to set the desired amount of dorsiflexion for the foot splint 10.

Figure 5:
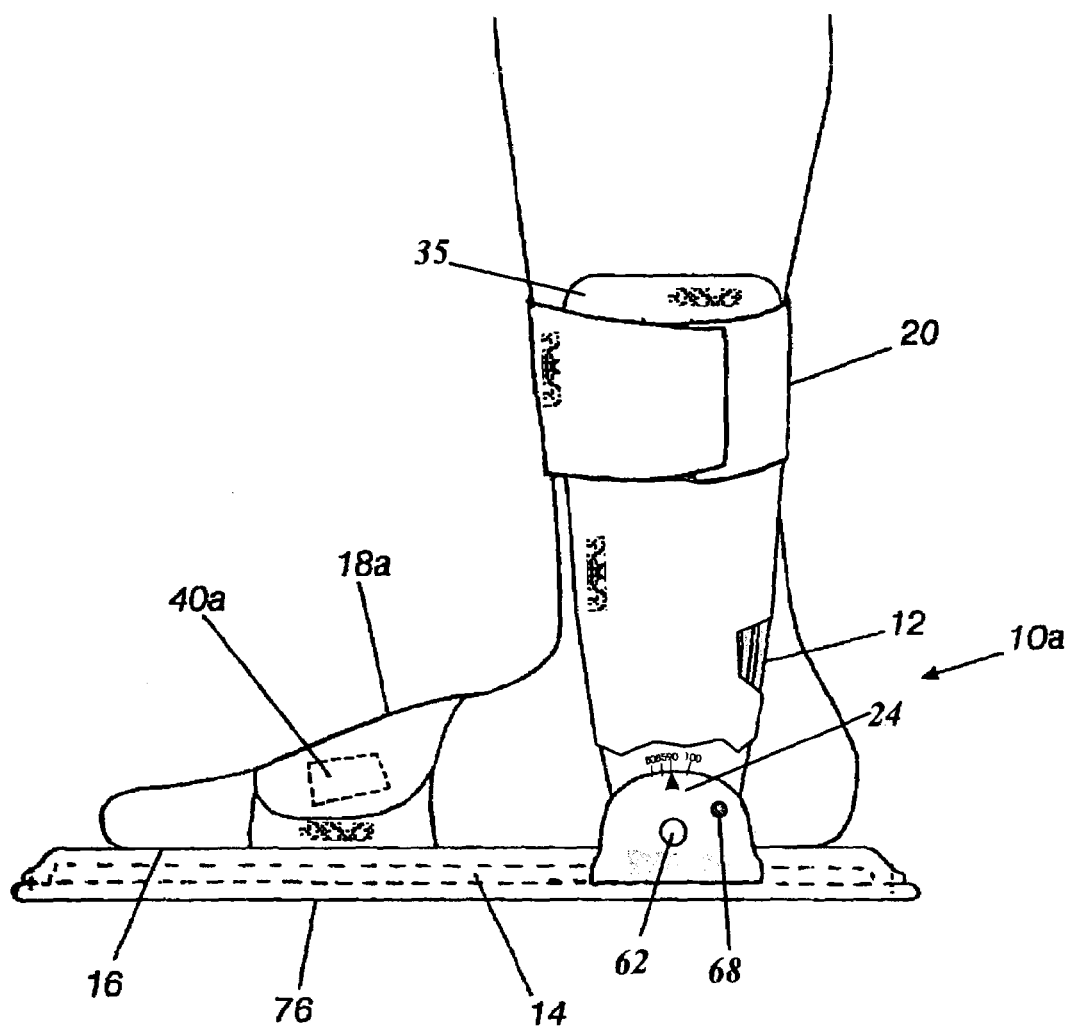
FIG. 5 is a side view of an alternative embodiment of a foot splint, taken from the side of the wearer's foot, in position on the wearer's foot.

FIG. 5 shows an alternative embodiment of a foot splint 10a. The alternative foot splint 10a is essentially the same as previously described, except that instead of having a full wrap, there is an open toe-open heel wrap 18a with an open toe flap 34a. The open toe flap 34a is pulled over the wearer's foot and secured by a Velcro-type hook fastener 40a to the open toe flap 34a having an outside Velcro pile material 42a. The open toe wrap 18a holds the wearer's foot along the footplate 14. This open construction, wherein much of the wearer's foot is not enclosed, assists in keeping the foot cool and comfortable. A suitable bottom 76 may be applied to the bottom of the footplate 14 to cushion the environment from the footplate 14. The strut is substantially removably enveloped by strut sleeve 35. The strut partially protrudes from the sleeve at the lower end 35l, which overlaps the axial rod 62 at the pivot point.

Figure 6:
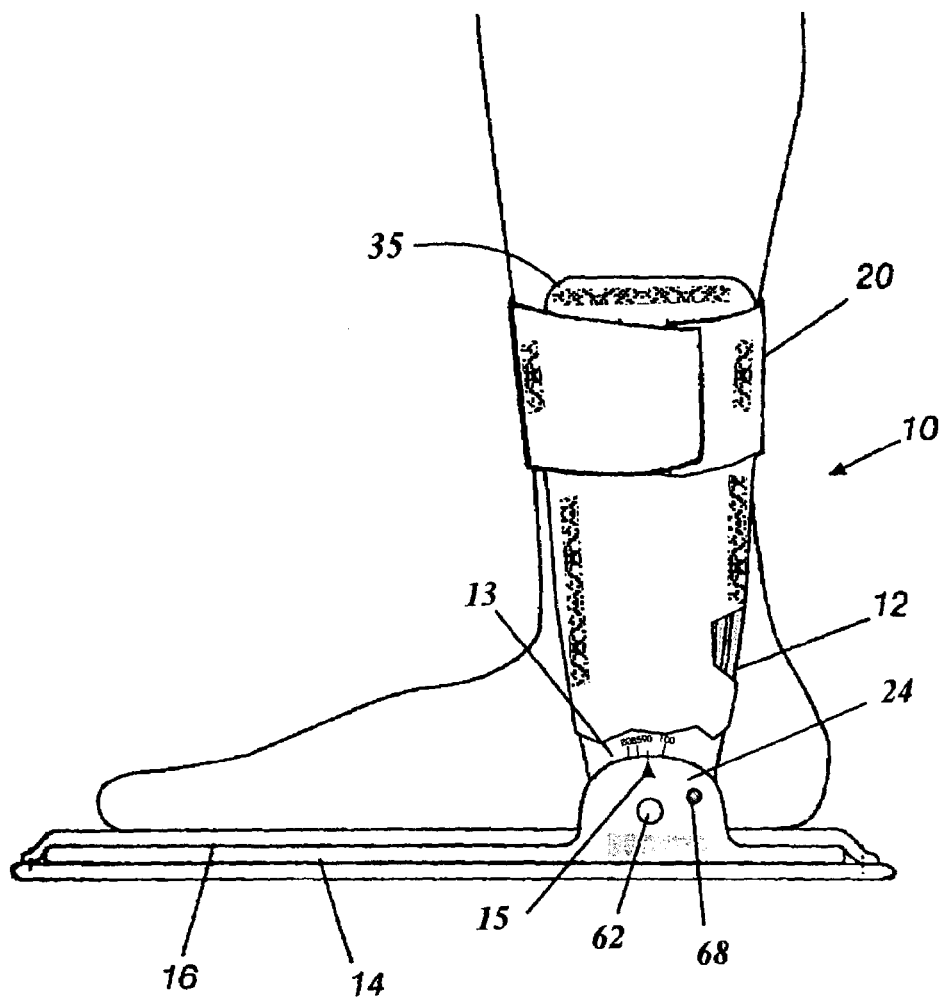
FIG. 6 is a side view of the foot splint, wherein the sides of the wrap are removed.

FIG. 6 illustrates that similarly the alternative embodiment can select the desired angled preset using indices 13 on the strut 12 and a pointer 15 on the bracket 24, and then setting the engaging locking means 68; or select the desired angled preset by visually aligning the holes 66 on the strut with hole 28 on the bracket and then setting the engaging locking means 68.

Referring to FIG. 3, in use, the flap portion 34 of the wrap 18 is pulled opened to allow easy placement of the wearer's foot onto the insole 16, where it is supported by the footplate 14. The desired degree of dorsiflexion for the foot splint 10 is then set by inserting the set screw 68 (FIG. 4) through corresponding set openings. Thereafter, the wearer secures the foot splint 10 in place on his foot and leg by first pulling the flap 34 over his foot and then securing the strap 70 around his leg. The flap 34 and strap 20 are held in place by Velcro™ hook and pile fasteners. The foot splint 10, now secured in place, holds the wearer's ankle in dorsiflexion, causing the wearer's plantar fascia to be held at a slight stretch. Similarly, the wearer secures the open toe-open heel wrap 18a on foot splint 10a in place on his foot and leg by first pulling the flap 34a over his foot and then securing the strap 20 around his leg. The flap 34a is held in place by Velcro™ hook fastener 40a to the pile material 42a comprising the outside material of the open toe-open heel wrap 18a; and the hook fastener 78 on the strap 20 is secured to the pile material.

The light weight, open configuration of the foot splint 10 allows the wearer to move substantially unimpeded between sleep positions, resulting in a more restful sleep. Moreover, the footplate 14 and the strut 12 provide sufficient structure to support the foot, yet are positioned on the wearer's foot and leg so that virtually no pressure points are caused to the wearer during periods of sleep. The malleolus opening 82 in the strut 12 further assists in eliminating pressure points by removing rigid structure from near the wearer's ankle.

The foot splint 10 is also comfortable since it requires only minimal structure to hold the wearer's foot in place. Moreover, the padded wrap 18, secures the foot within the foot splint 10 while minimally confining the foot and forming a slipper-like feel for the wearer.

Figure 7:
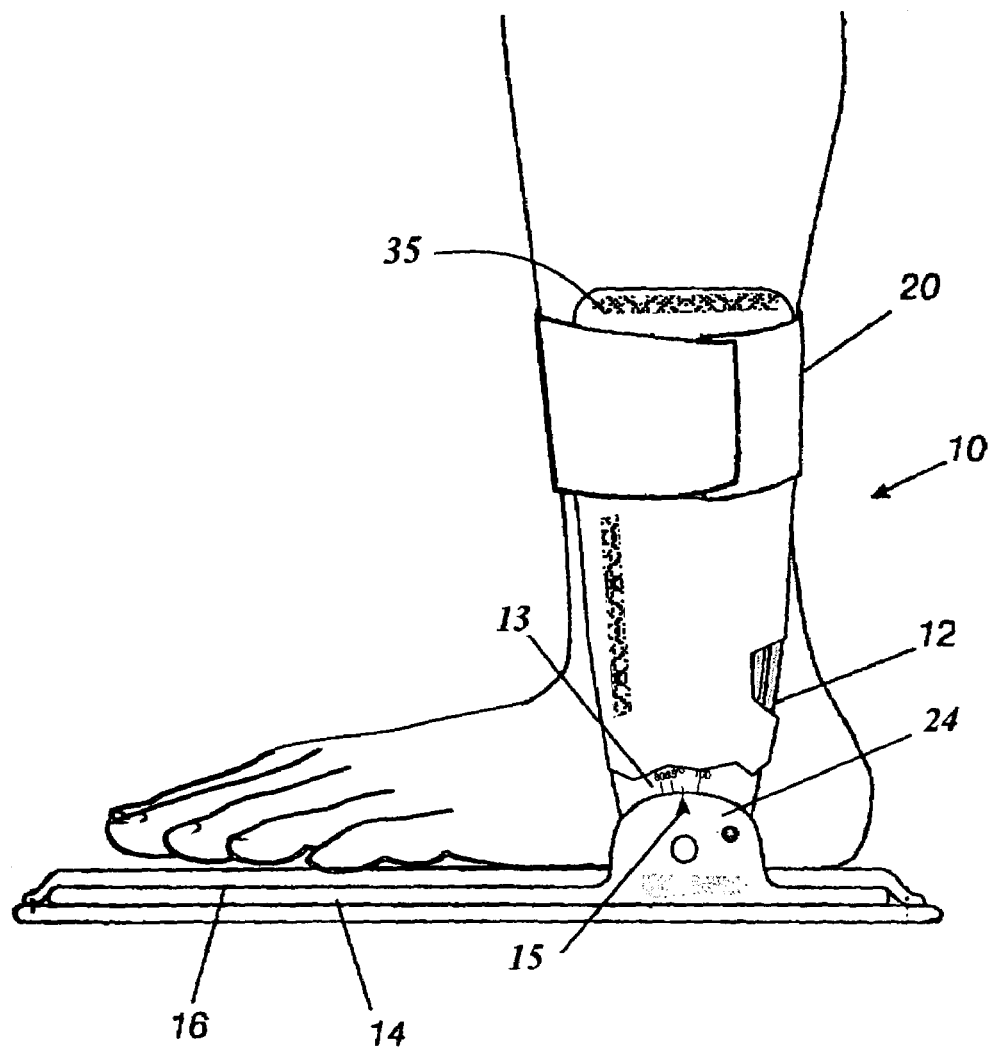
FIG. 7 is a side view of the foot splint having a lateral strut, in position on the wearer's left foot, wherein the sides of the wrap are removed.

The foot splint embodiments shown in FIGS. 1-6 have a medial strut attached to the medial side (inside) of the foot, however the invention is not to be construed as so limited. In FIG. 7 the foot splint 10 has a lateral strut 12 having a malleolus opening 82, the lateral strut 12 is recessed such that it has a lessened chance of hitting the wearer's other leg. However, the foot splint 10, 10a may be configured with only a lateral strut, or having both a medial and a lateral strut. Without need for further description, one skilled in the subject art would appreciate that the lateral strut could be similarly configured to that of the medial strut. The foot splint configured to have the strut on the lateral side is comprised of a footplate having a lateral side, a medial side, a toe region and a heel region; a bracket, integrally attached to the footplate on the lateral side at the heel region. The bracket has at least one ankle angle preset; a strut having an upper region and a lower region, and a plurality of radially spaced angle presets. The strut is pivotally attached to the bracket, and is removably enveloped by a strut sleeve with an integral adjustable leg strap. The strut sleeve has an upper end, and a lower end. The strut protrudes from the sleeve at the lower end. The adjustable leg strap attached to the upper end of the strut sleeve. The strap secures the upper end to the leg of a wearer during operation.

It is to be understood that the foregoing description and specific embodiments are merely illustrative of the best mode of the invention and the principles thereof, and that various modifications and additions may be made to the apparatus by those skilled in the art, without departing from the spirit and scope of this invention, which is therefore understood to be limited only by the scope of the appended claims.

What is claimed is:

1. A foot splint for treating foot and ankle injuries comprising:
    a footplate having a lateral side, a medial side, a toe region and a heel region;
    a bracket, integrally attached to said footplate on said medial side at said heel region, said bracket having at least one ankle angle preset;
    a strut having an upper region and a lower region, and comprising a plurality of radially spaced angle presets, said strut being pivotally attached to said bracket;
    a strut sleeve removably enveloping said strut, said sleeve comprising an upper end, and a lower end, said strut protruding from said sleeve at said lower end;
    an adjustable leg strap attached to said strut sleeve at said upper end, said strap securing said upper region of the strut to the leg of a wearer during operation.

2. The foot splint according to claim 1, wherein said adjustable leg strap has hook and pile fasteners.

3. The foot splint according to claim 1, wherein said plurality of radially spaced angle presets comprises angle settings of about 90, 85 and 80 degrees.

4. The foot splint according to claim 1, wherein said strut has an opening for the malleolus.

5. The foot splint according to claim 1, further comprising a padded insole that provides a cushioning barrier between the foot and the footplate.

6. The foot splint according to claim 1, further comprising a wrap for holding the foot in place on the footplate.

7. The foot splint according to claim 1, wherein the plurality of angled presets is marked using indices on the strut and a pointer on the bracket.

8. The foot splint according to claim 6, wherein said wrap further comprises a cupped heel portion to hold the heel of the wearer's foot.

9. The foot splint according to claim 6, wherein the wrap is an open-toe open-heel wrap.

10. A foot splint for treating foot and ankle injuries comprising:
    a footplate having a lateral side, a medial side, a toe region and a heel region;
    a bracket, integrally attached to said footplate on said lateral side at said heel region, said bracket having at least one ankle angle preset;
    a strut having an upper region and a lower region, and comprising a plurality of radially spaced angle presets, said strut being pivotally attached to said bracket;
    a strut sleeve removably enveloping said strut, said sleeve comprising an upper end, and a lower end, said strut protruding from said sleeve at said lower end;
    an adjustable leg strap attached to said strut sleeve at said upper end, said strap securing said upper region of the strut to the leg of a wearer during operation.

11. The foot splint according to claim 10, wherein said adjustable leg strap has hook and pile fasteners.

12. The foot splint according to claim 10, wherein said plurality of radially spaced angle presets comprises angle settings of about 90, 85 and 80 degrees.

13. The foot splint according to claim 10, wherein said strut has an opening for the malleolus.

14. The foot splint according to claim 10, further comprising a padded insole that provides a cushioning barrier between the foot and the footplate.

15. The foot splint according to claim 10, further comprising a wrap for holding the foot in place on the footplate.

16. The foot splint according to claim 10, wherein the plurality of angled presets is marked using indices on the strut and a pointer on the bracket.

17. The foot splint according to claim 15, wherein said wrap further comprises a cupped heel portion to hold the heel of the wearer's foot.

18. The foot splint according to claim 15, wherein the wrap is an open-toe open-heel wrap.

19. A foot splint for treating foot and ankle injuries comprising:
    a footplate having a lateral side, a medial side, a toe region and a heel region;
    a lateral bracket, integrally attached to said footplate on said lateral side at said heel region, said bracket having at least one ankle angle preset;
    a medial bracket, integrally attached to said footplate on said medial side at said heel region, said bracket having at least one ankle angle preset;
    a lateral strut having an upper region and a lower region, and comprising a plurality of radially spaced angle presets, said strut being pivotally attached to said lateral bracket;
    a medial strut having an upper region and a lower region, and comprising a plurality of radially spaced angle presets, said medial strut being pivotally attached to said medial bracket;

medial and lateral strut sleeves removably enveloping said medial and lateral struts, said sleeves comprising an upper end, and a lower end, said struts protruding from said medial and lateral sleeves at said lower end; and an adjustable leg strap attached to either the medial or the lateral strut sleeve at said upper end of said strut sleeve, said strap securing said upper region of the strut to the leg of a wearer during operation.

20. The foot splint according to claim 19, wherein said plurality of radially spaced angle presets comprises angle settings of about 90, 85 and 80 degrees.

* * * * *